United States Patent [19]

Kleinstreuer

[11] Patent Number: 4,636,473

[45] Date of Patent: Jan. 13, 1987

[54] MEMBRANE AND STATIC MIXER-MODERATED BIOREACTOR WITH ANTI-FOULING DEVICE

[75] Inventor: Clement Kleinstreuer, Troy, N.Y.

[73] Assignee: Rensselaer Polytechnic Institute, Troy, N.Y.

[21] Appl. No.: 539,566

[22] Filed: Oct. 6, 1983

[51] Int. Cl.⁴ .................. C12M 1/36; C12M 1/34; C12M 1/12; C12M 1/02
[52] U.S. Cl. ..................... 435/289; 435/291; 435/311; 435/316; 435/284; 435/813; 435/315; 210/108; 210/138; 210/234; 210/321.1; 210/433.2
[58] Field of Search ............ 435/3, 287, 288, 289, 435/291, 311, 313, 315, 316, 284, 285, 286, 813, 819; 210/650, 651, 108, 137, 138, 321.1, 433.2, 636, 637, 234; 55/482

[56] References Cited

U.S. PATENT DOCUMENTS

| | | | |
|---|---|---|---|
| 3,186,917 | 6/1965 | Gerhardt et al. | 435/244 |
| 3,275,528 | 9/1966 | Ainis | 435/284 X |
| 3,286,992 | 11/1966 | Armeniades | 261/D 26 X |
| 3,630,362 | 12/1971 | Matthews | 210/108 |
| 3,638,793 | 2/1972 | Peck | 210/108 X |
| 3,645,400 | 2/1972 | Floyd | 210/108 |
| 3,734,851 | 5/1973 | Matsumura | 210/646 X |
| 3,868,322 | 2/1975 | Orloff | 210/108 |
| 3,962,042 | 6/1976 | Malick | 435/314 |
| 4,225,671 | 9/1980 | Puchinger et al. | 435/240 X |
| 4,241,187 | 12/1980 | White | 210/321.2 X |
| 4,251,633 | 2/1981 | Orlowski et al. | 435/813 X |
| 4,357,424 | 11/1982 | Bu'Lock | 435/314 X |
| 4,385,113 | 5/1983 | Chappelle et al. | 435/289 X |
| 4,411,792 | 10/1983 | Babb | 210/651 |
| 4,482,461 | 11/1984 | Hindman et al. | 210/108 X |

FOREIGN PATENT DOCUMENTS

| | | | |
|---|---|---|---|
| 0166985 | 10/1982 | Japan | 435/288 |
| 0830512 | 3/1960 | United Kingdom | 210/108 |
| 1223418 | 2/1971 | United Kingdom | 435/315 |
| 0759586 | 8/1980 | U.S.S.R. | 435/314 |

OTHER PUBLICATIONS

English Translation Japanese Patent 0,166,985 published Oct. 14, 1982.

Primary Examiner—Robert J. Warden
Assistant Examiner—Randall E. Deck
Attorney, Agent, or Firm—McGlew and Tuttle

[57] ABSTRACT

A bioreactor arrangement comprises a housing defining a closed space having a longitudinal axis with at least two spaced apart microporous membranes fixed therein dividing the space into a first chamber on one side of one of the membrane, a second chamber on one side of the other membrane, and a third chamber between opposite sides of the one and other membrane. The housing includes at least one port communicating with each chamber and fixed static mixers in the form of curved and/or perforated members in the third chamber. The first and second chambers are used alternately to receive and discharge material in the bioreactor. The third chamber contains an active substance which produces a useful product from raw materials in the supplied fluid. A flow valve and pump are provided for selectively supplying fluid carrying raw material to one or the other of the first and second chambers. The flow through the housing is reversed after a selected period of time or after a selected pressure level has been reached in the housing to avoid fouling of membrane surfaces and prevent the formation of any appreciable caked substance on any membrane surface. Additional ports are provided to the first and second chambers and connected over valves for discharging products.

5 Claims, 6 Drawing Figures

MEMBRANE AND STATIC MIXER-MODERATED BIOREACTOR WITH ANTI-FOULING DEVICE

FIELD AND BACKGROUND OF THE INVENTION

The present invention relates, in general, to the field of continuous operation membrane compartmentalized biological reactors, and in particular, to a new and useful symmetrical operation reactor which automatically prevents concentration polarization and deposition layer formation (or fouling) on membrane surfaces and provides for gentle agitation of fragile particles.

In multi-phase flow biological or chemical reactor processes, certain constitutents have to be permanently separated from the mainstream solution while constantly being mixed. For example in bioreactors, enzymes, tissue cultures, or whole cells are entrapped in specific reactor compartments and gently agitated. Membranes of all types and shapes together with a variety of mixing devices have been utilized in modern reactor design in an attempt to achieve these goals. However, all membrane-moderated reactors suffer from concentration polarization and membrane fouling which in turn may cause flux reduction, higher energy expenditure, transients, membrane failure and/or disruption of the continuous process since at one point membrane cleaning by some physical or chemical means, is required. In addition, conventional mixing (e.g. with a stirrer) may cause mechanical destruction of the microorganisms. Until the membrane fouling problem is solved, the performance of membrane-moderated continuous flow reactors will be technically and economically inferior to conventional reactors such as stirred tanks with recycling or bubble columns.

With respect to biochemical reactors, a number of reactors using membranes to separate (or entrap) biocatalysts but allow nutrients to pass freely, are known. Some approaches to utilizing microorganisms to produce a product include the structure disclosed in U.S. Pat. No. 3,186,917 to Gerhard et al. A membrane is provided to pass a nutrient solution to a culture of microorganisms for producing a desired product.

U.S. Pat. No. 3,734,851 to Matsumura describes the use of two membranes with cells being maintained therebetween with flow of mass to and from the cells being accomplished through the respective membrane. U.S. Pat. No. 3,769,176 to Hise et al discloses the production of biochemicals by microorganisms and the like, wherein nutrients are supplied to the microorganisms and removed from the microorganisms by means of membranes. The following U.S. patents also describe these membranes in similar environments: U.S. Pat. No. 3,281,087 to Knazek et al; U.S. Pat. No. 3,915,802 to Kominek; amd U.S. Pat. No. 4,241,187 to White.

Designs and operational modes for innovative membrane chamber bioreactors which are of particular interest for the application of the present invention have recently been described in the article "Membrane Technology and Biotechnology", (1980) by A. S. Michaels, pp. 329–351, printed in the Netherlands by Elsevier Scientific Publishing Co., Amsterdam.

SUMMARY OF THE INVENTION

The present invention is drawn to a new anti-fouling device and static mixing mechanism which allows continuous, low-shear, almost maintenance-free operation of biochemical reactors with symmetric, membrane separated compartments.

The invention includes tow main parts, a bioreactor and an anti-fouling device.

The bioreactor of the present invention comprises a metal or plastic housing, i.e. a closed cylinder which is symmetrically subdivided by membranes into three or four chambers. Within the one or two center compartments, thin perforated concentric tubes or static mixers secure gentle mixing of the fermentation broth. The static mixer-membrane unit is an exchangeable cartridge which can be easily inserted into or removed from the main housing.

The anti-fouling device comprises an arrangement of valves and feed/product lines which allow continuous flow bioreactor operation in a symmetrical fashion. The substrate plus nutrients, and air if desired, are pumped via a 3-way valve either into the left or right end compartment depending on a signal from a pressure transducer or timer. After a prescribed pressure level or time interval is reached, the convective flow direction is reversed. Excess substrate solution can be recycled into a reservoir. Both end chambers have effluent valves for the product stream, one of which is either open or closed depending on the direction of flow.

The objectives and advantages of the present invention include: (i) mixing without moving parts, i.e. low technology reactor; (ii) gentle agitation to avoid high shear stresses on fragile microbes, in particular genetically engineered microorganisms, enzymes and tissue cultures; (iii) use of two different biocatalysts in series and the possibility of entrapment or immobilization of cells/enzymes; (iv) lower energy consumption and continuous operation due to anti-fouling devices; (v) no diffusion limitation due to prevention of cake layer formation on membranes; (vi) maintenance of clean membranes to avoid possible membrane alteration or destruction; and (vii) low initial capital cost.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION IN THE DRAWINGS

DESCRIPTION OF THE PREFERRED EMBODIMENTS

Figure 1:
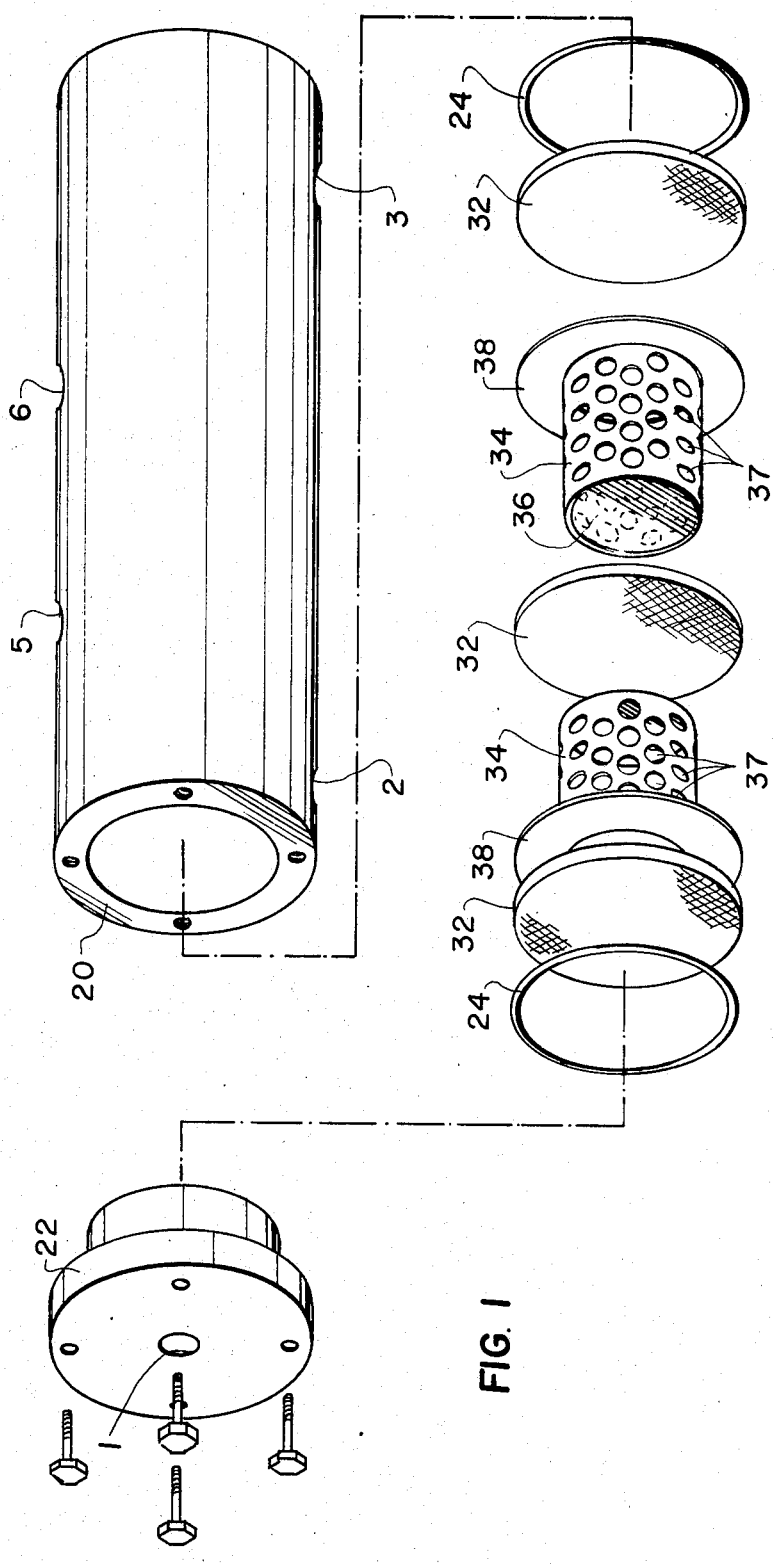
FIG. 1 is an exploded perspective view of the biochemical reactor in accordance with the invention.
Figure 2:
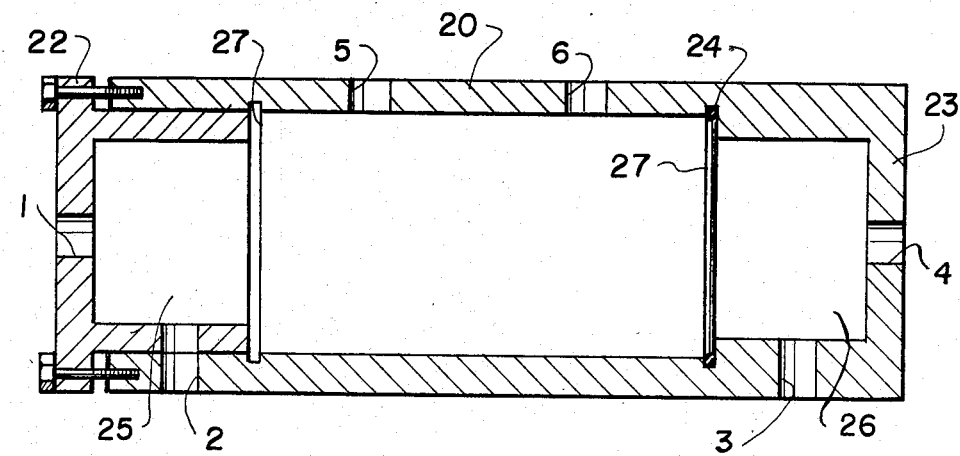
FIG. 2 is a sectional view of the reactor housing without a mixer-membrane cartridge.

Referring to the drawings in particular, the invention embodied therein, in FIGS. 1 through 6, comprises a membrane bioreactor generally designated 10 with low-shear mixing and anti-fouling devices generally designated 12 and 14, respectively. The reactor includes a cylindrical housing 20 and a top cover 22 which, when screwed onto the housing 20, pressure-seals any reactor cartridge (30 in FIGS. 3, 4 and 5) using two O-rings 24. Housing 20 has a closed end 23 and defines two shoulders 27,27 for seating O-rings 24,24.

Figure 3:
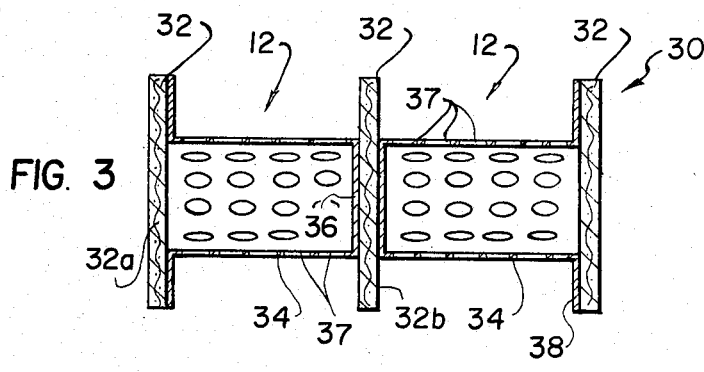
FIG. 3 is a sectional view of one embodiment of a cartridge.
Figure 4:
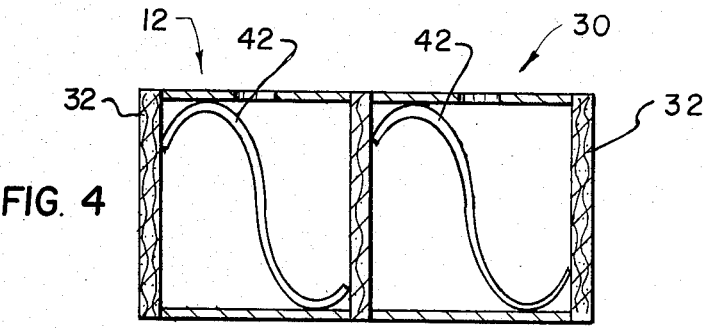
FIG. 4 is a view similar to FIG. 3 of another cartridge embodiment.
Figure 5:
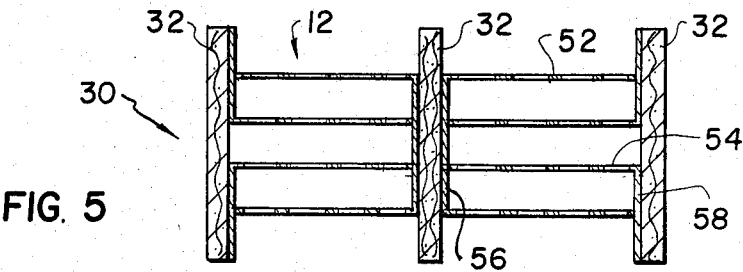
FIG. 5 is a view similar to FIG. 3 of still another cartridge embodiment.
Figure 6:
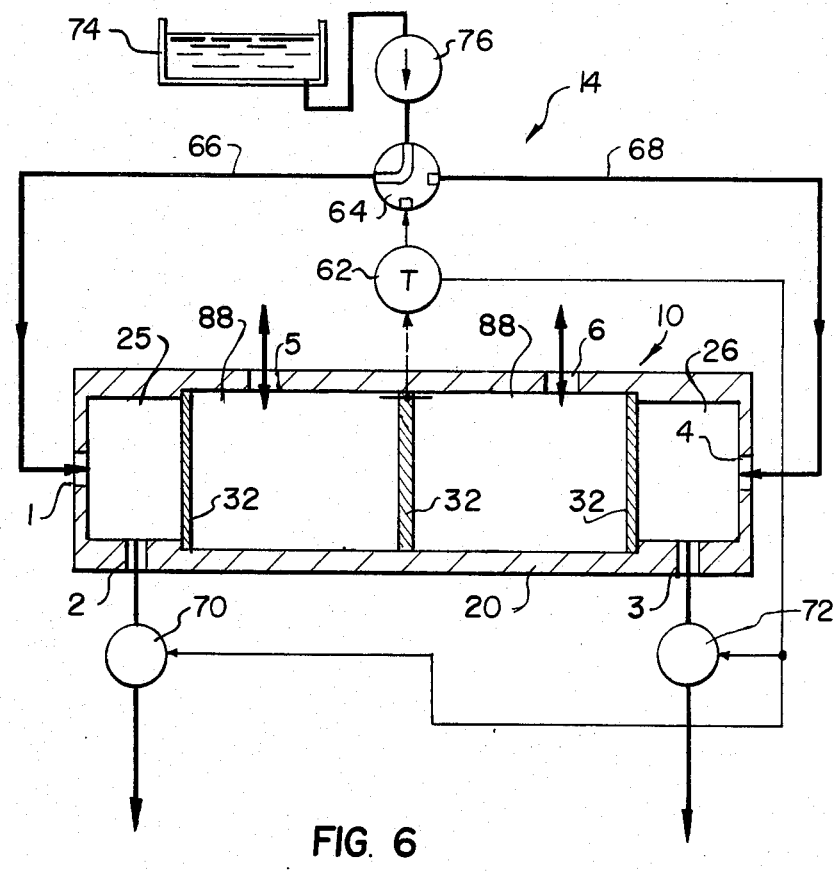
FIG. 6 is a schematic view of the anti-fouling device with its arrangement of valve and feeding/product lines.

In FIG. 3, a reactor cartridge 30 which fits easily into the housing 20, is shown as a loose, self-centering assembly of three membranes 32 and two or more static mixing devices 12 made out of sheet metal, plastic or ceramic. Each device comprises a cylinder 34 with perforations 37 forming static mixers. These mixing devices are fixed surface members. The solution, i.e. solvent (water), bases (oxygen if desired), substrate nutrients and biocatalysts, are driven by an axisymmetric pressure gradient (to be explained with reference to FIG. 6) along the curved and through the perforated static mixers 34 and are thereby gently agitated separately in each center chamber defined between membranes 32. The two center chambers may contain different biocatalysts. As shown in FIG. 4, the mixing devices could also be fixed solid curved surface members 42, which extend partly across each chamber so that fluid moves over and around surface members 42. Additional perforated concentric cylinders, to immobilize and grow enzymes and the like can be used as shown in FIG. 5 at 52 and 54 where cylinder 54 is a second perforated cylinder that is positioned radially inwardly of perforated cylinder 52. The microporous membranes 32 act as semi-permeable barriers which retain the biocatalysts only. The reactor has a vertical symmetry which allows convective flow operation from left to right and vice-versa. For example, with reference to FIG. 6, based on a set time interval or a pressure level in the center chambers, a timer or transducer 62 (control means) triggers valve 64 which closes the feed line 66 connected to a port 1 in cover 22 and directs the substrate solution into a former outlet chamber 26 of housing 20 via a port 4 and line 68. At the same time, a signal from 62 opens a valve 70 (product effluent stream) at a port 2 of a chamber 25 and shuts a valve 72 at a port 3 of chamber 26. Any concentration boundary layer at the left membrane surfaces (FIG. 6) will be immediately destroyed. If any measurable pressure builds up due to deposition layer formation on the other membrane surfaces (right surfaces in FIG. 6), the direction of the substrate solution flow is reversed, using valve 64. This build-up is measured by transducer 62 or assumed to take place during a settable time period in which case 62 is a timer.

Valve 64 is advantageously a three-way valve which can supply the fluid for carrying the nutrient or other necessary raw material from reservoir 74 by way of pump 76 to either line 66 or line 68.

The product is tapped from either chamber 25 or 26 (depending on the flow direction) through port 2 and 3 using product valves 70 and 72 which are controlled by the timer/transducer 62 as noted above.

In addition to ports 1 through 4, the middle chambers 88 are each provided with a port 5 and 6 which is useable for aeration and/or degassing of the active materials within chambers 88. These same ports can be used to charge the chambers with these active ingredients.

The specific microbes, enzymes or other active material in chambers 88, as well as the nutrient or other fluids to be supplied by pump 76 are not here described in detail.

The present invention is drawn primarily to the reactor and connected equipment as well as the method of avoiding fouling. Details concerning specific active ingredients, nutrients, raw materials and products can be found in the above-identified prior art.

The membranes 32 in the various cartridge embodiments of the invention are also known and can include microporous materials, such as ceramic, metal or polypropylene layers with supports, such as metal screens or grids. Such supported membranes are also known in the art.

As shown in the embodiments of FIGS. 3 and 4, the perforated cylinders 34, 52 or 54 may include a rim on one side and a close surface on an opposite side.

In the embodiment of FIG. 3, for example, perforated cylinders 34 each have a closed end 36 and a flanged end 38 without perforations. In the embodiment of FIG. 5, the flanged end 58 extends over the ends of both perforated cylinders 52, 54 as does the the covered end 56.

The result of this structure is that, referring back to FIG. 3, the central area 32a of the left-most membrane 32 is utilized since the outer portions are covered by ring or flange 38. The outer peripheral area 32b of the central membrane 32 is utilized since the middle area of this membrane is covered by portion 36 of perforated cylinder 34. In a similar fashion, the central areas of the outer membranes 32 in FIG. 5 are exposed while the outer peripheral areas of the center membrane in FIG. 5 is exposed. After a prolonged period of use, the addition of one of the outer membranes can be shifted with that of the central membrane so that the previously unused portions are then utilized. Since there is only a single central membrane in each of the embodiments shown, a simple rotation scheme can be utilized or fresh membranes may be added as needed.

While specific embodiments of the invention have been shown and described in detail to illustrate the application of the principles of the invention, it will be understood that the invention may be embodied otherwise without departing from such principles.

What is claimed is:

1. A bioreactor apparatus comprising:

a housing defining a closed space and having a longitudinal axis;

first and second spaced-apart microporous membranes fixed in said space and dividing said space into a first chamber on one side of one of said first and second membranes, a second chamber on one side of the other of said first and second membranes, and a third chamber between opposite sides of said one and other first and second membranes, said longitudinal axis of said housing extending through said first membranes and through said first, second and third chambers;

said housing including a first port communicating with said first chamber and a second port communicating with said second chamber;

a third microporous membrane extending in said third chamber dividing said third chamber into two sections, said third microporous membrane having opposite sides facing said opposite sides of said one and other first and second membranes, said first and second membranes and said third membrane extending radially in said housing with respect to said longitudinal axis thereof;

a perforated cylinder disposed in each of said two two sections, each perforated cylinder having a cylindrical portion with an axis parallel to said longitudinal axis of said housing and being spaced radially inwardly from said housing, each cylindrical portion having a cover at one end thereof engaged with said third membrane and a radially outwardly extending flange at an opposite end thereof engaged with one of said first and second membranes, said cover and flange of each perforated cylinder being without perforations and said perforated cylindrical portion of each perforated cylinder functioning to agitate contents of said two sections of said third chamber;

a first line for carrying a fluid to said first chamber connected to said first port;

a second line for carrying fluid to said second chamber connected to said second port;

valve means connected to said first and second lines for selectively supplying fluid to said first and second lines;

pump means connected to said valve means for pumping fluid through said valve means to one of said first and second lines; and control means connected to said valve means for activating said valve means to alternately and selectively supply fluid to one of said first and second lines and then to the other of said first and second lines in response to a selected time interval whereby flow of fluid through said first, second and third chambers alternates in a direction to avoid fouling of said one and opposite sides of each of said first and second microporous membranes.

2. An apparatus according to claim 1, wherein said housing includes a third port communicating with said first chamber and a fourth port communicating with said second chamber, a first valve connected to said third port and a second valve connected to said fourth port, each valve connected to said control means for selective operation thereof to open said second valve when said valve means is operated to supply fluid to said first chamber and to open said first valve when said valve means is operated to supply fluid to said second chamber.

3. An apparatus according to claim 2, wherein said housing includes a fifth port communicating with said third chamber for aerating or degassing said third chamber.

4. An apparatus according to claim 1, wherein said valve means comprises a three-way valve having one connection connected to said pump means, a second connection connected to said first line and a third connection connected to said second line.

5. An apparatus according to claim 4, wherein said control means comprises a timer.

* * * * *